United States Patent
Ben-Ari et al.

(10) Patent No.: US 10,201,507 B2
(45) Date of Patent: Feb. 12, 2019

(54) MODULATORS OF INTRACELLULAR CHLORIDE CONCENTRATION FOR TREATING FRAGILE X SYNDROME

(71) Applicants: NEUROCHLORE, Marseilles (FR); INSERM (INSTITUT NATIONAL DE LA SANTÉ ET DE LA RECHERCHE MÉDICALE), Paris (FR); UNIVERSITE AIX MARSEILLE, Marseilles (FR); CENTRE HOSPITALIER UNIVERSITAIRE DE BREST, Brest (FR)

(72) Inventors: Yehezkel Ben-Ari, La Ciotat (FR); Eric Lemonnier, Brest (FR); Nail Burnashev, Marseilles (FR); Roman Tyzio, Marseilles (FR)

(73) Assignees: NEUROCHLORE, Marseilles (FR); INSERM (INSTITUT NATIONAL DE LA SANTE ET DE LA RECHERCHE MEDICALE), Paris (FR); UNIVERSITE AIX MARSEILLE, Marseilles (FR); CENTRE HOSPITALIER UNIVERSITAIRE DE BREST, Brest (FR)

( * ) Notice: Subject to any disclaimer, the term of this patent is extended or adjusted under 35 U.S.C. 154(b) by 93 days.

(21) Appl. No.: 14/443,154

(22) PCT Filed: Nov. 15, 2013

(86) PCT No.: PCT/EP2013/073942
§ 371 (c)(1),
(2) Date: May 15, 2015

(87) PCT Pub. No.: WO2014/076235
PCT Pub. Date: May 22, 2014

(65) Prior Publication Data
US 2015/0335600 A1 Nov. 26, 2015

Related U.S. Application Data

(60) Provisional application No. 61/727,235, filed on Nov. 16, 2012.

(30) Foreign Application Priority Data

Nov. 16, 2012 (EP) .................................. 12193087

(51) Int. Cl.
| A61K 38/00 | (2006.01) |
| A61K 47/00 | (2006.01) |
| A61K 31/00 | (2006.01) |
| A61K 38/11 | (2006.01) |
| A61K 31/196 | (2006.01) |
| A61K 31/7088 | (2006.01) |

(52) U.S. Cl.
CPC ............ *A61K 31/00* (2013.01); *A61K 31/196* (2013.01); *A61K 31/7088* (2013.01); *A61K 38/11* (2013.01)

(58) Field of Classification Search
USPC .......................................................... 514/1.2
See application file for complete search history.

(56) References Cited

U.S. PATENT DOCUMENTS

| 3,985,777 | A | 10/1976 | Feit |
| 4,247,550 | A | 1/1981 | Feit |
| 7,282,519 | B2 | 10/2007 | Garvey |
| 2007/0155729 | A1 | 7/2007 | Morgan |
| 2008/0124709 | A1* | 5/2008 | Huang ................. C12Q 1/6827 435/6.12 |
| 2008/0139472 | A1* | 6/2008 | Lauterborn ........ A61K 31/4525 514/8.4 |

FOREIGN PATENT DOCUMENTS

| AU | 2011236093 | 11/2011 |
| EP | 2433635 | 3/2012 |
| GB | 2207129 | 1/1989 |
| WO | 2006-110187 | 10/2006 |
| WO | WO 2006/110187 | * 10/2006 |
| WO | 2009-097695 | 8/2009 |
| WO | 2009-114950 | 9/2009 |
| WO | 2010-132999 | 11/2010 |
| WO | 2011-011692 | 7/2011 |
| WO | 2012-018635 | 2/2012 |
| WO | 2012-019990 | 2/2012 |

OTHER PUBLICATIONS

Taylor et. al. (Journal of Medicinal and Pharmaceutical Chemistry (1962) 5:312-320).*
Tyzio et al., "Maternal oxytocin triggers a transient inhibitory switch in GABA signaling in the fetal brain during delivery," 2006 Science 314, 1788.
Tyzio et al, "Postnatal changes in somatic gamma-aminobutyric acid signalling in the rat hippocampus," 2008, Eur J Neurosci. 27(10):2515-228.
Adusei et al., "Early developmental alterations in GABAergic protein expression in fragile X knockout mice," Neuropharmacology. Sep. 2010;59(3):167-171.
Gagnon et al., "Characterization of SPAK and OSR1, regulatory kinases of the Na—K—2Cl cotransporter," 2006 Mol. Cell. Biol. 26(2):689-698.
Lemonnier et al., "Treating Fragile X syndrome with the diuretic bumetanide: a case report," Acta Paediatr. Jun. 2013;102(6):e288-290.
Hall et al., "Effects of intranasal oxytocin on social anxiety in males with fragile X syndrome," Psychoneuroendocrinology. Apr. 2011;37(4):509-518.
Torrioli et al., "Treatment with valproic acid ameliorates ADHD symptoms in fragile X syndrome boys," Am J Med Genet A. Jun. 2010;152A(6):1420-1427.

(Continued)

Primary Examiner — Marcos L Sznaidman
(74) Attorney, Agent, or Firm — Young & Thompson

(57) ABSTRACT

A composition for treating Fragile X syndrome in a subject in need thereof, wherein the composition includes an effective amount of a modulator of a chloride transporter.

10 Claims, 5 Drawing Sheets

(56) References Cited

OTHER PUBLICATIONS

Lemonnier et al., "The diuretic bumetanide decreases autistic behaviour in five infants treated during 3 months with no side effects," Acta Paediatr. Dec. 2010;99(12):1885-1888.
Ben-Ari et al., "The GABA excitatory/inhibitory shift in brain maturation and neurological disorders," Neuroscientist. Oct. 2012;18(5):467-486.
International Search Report, dated Mar. 25, 2014; Application PCT/EP2013/073942.

* cited by examiner

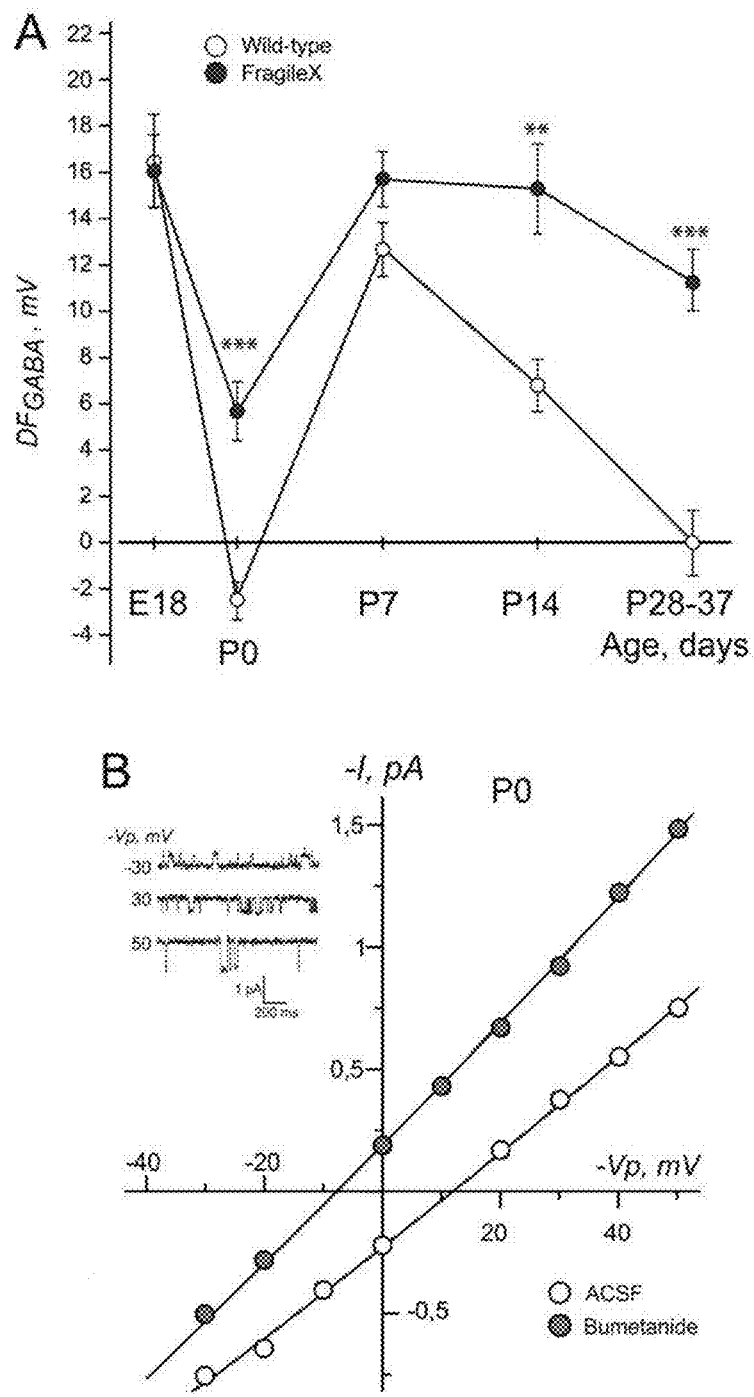
FIG. 1A-B

MODULATORS OF INTRACELLULAR CHLORIDE CONCENTRATION FOR TREATING FRAGILE X SYNDROME

FIELD OF INVENTION

The present invention relates to the treatment of Fragile X syndrome. More specifically, the present invention relates to a method for treating Fragile X syndrome in a subject in need thereof, wherein said method comprises modulating the intracellular level of chloride, such as, for example, by administering to the subject a modulator of a chloride transporter.

BACKGROUND OF INVENTION

Fragile X syndrome is the most common inherited form of mental retardation, affecting about 1 in every 4000 boys and about 1 in every 8000 girls.

Fragile X syndrome (FXS) is a genetic disorder caused by the expansion of a CGG trinucleotide repeat in the 5' untranslated region (5'-UTR) of the Fragile X mental retardation 1 (FMR1) gene, which is located on the X chromosome. The mutation results in a reduced or absent expression of the Fragile X mental retardation protein (FRMP). Even if the exact function of FRMP is not known, experimental evidences have shown that its normal expression is required for normal neural development.

Depending at least in part on the length of the CGG repeat expansion, FXS patients will present various degrees of symptoms severity. Major symptoms associated with FXS are mental retardation and learning disabilities, in particular delays in learning how to sit, walk and talk. As a consequence, FXS patients usually present nervous or cluttered speech. Moreover, FXS patients may have deficient central executive, working, phonological and/or visual-spatial memories; or difficulty with face encoding.

Behavioral and emotional problems may also be encountered, such as, for example, hyperactivity, stereotypy, anxiety, seizures, impaired social behavior, cognitive delay, irritability, aggression or self-injurious behavior. Moreover, FXS may also cause ophthalmologic problems including strabismus, and recurrent otitis media and sinusitis during early childhood.

Due to the high prevalence of Fragile X syndrome, there is a real need for a specific treatment.

The patent application EP 2 433 635 describes the use of PAK (p21-activated kinases) modulators for treating Fragile X syndrome.

The patent application WO2012/019990 describes the use of glutamate 5 receptor (mGlu5) antagonists for the treatment of Fragile X syndrome.

The patent application AU 2011 236093 describes the use of a gamma-aminobutyric acid agonist, in particular of Baclofen, for treating Fragile X syndrome. The drug STX209, a baclofen derivative, is currently under clinical trial for determining its efficacy, safety, and tolerability for the treatment of social withdrawal in adolescents and adults with Fragile X syndrome.

Other clinical trials are currently in progress, such as, for example, with AFQ056 (a mGluR5 antagonist developed by Novartis), minocycline hydrochloride (an antibiotic which may lower matrix metalloproteinase 9 (MMP9) levels) or Acamprosate (an agonist of a GABA receptor).

However, to the Applicant knowledge, there is currently no drug treatment with prove efficacy for Fragile X syndrome.

The Applicant surprisingly showed that the intracellular chloride level was significantly increased in a mouse model of FXS as compared to the wild-type situation, leading to an abnormal neuronal activity (see Examples). This was surprising as Adusei et al (2010 Neuropharmacology 59:167-171) disclose that the chloride transporters NKCC1 and KCC2 are not involved in FXS.

The present invention thus relates to the use of a modulator of intracellular chloride levels, in particular inhibitor of NKCC or activator of KCC, for treating FXS in a subject in need thereof.

SUMMARY

The present invention thus relates to a composition for treating Fragile X syndrome in a subject in need thereof, wherein said composition comprises an effective amount of a modulator of a chloride transporter. In one embodiment, said modulator of chloride transporter is not valproic acid, oxytocin, bendroflumethiazide, benzthiazide, buthiazide, chlorothiazide, cyclothiazide, epithiazide, metalthiazide, hydrochlorothiazide, hydro-flumethiazide, methylclothiazide, polythiazide, trichlormethiazide, chlorthalidone, indapamide, metolazone and quinethazone.

In one embodiment of the invention, said modulator is an inhibitor of a transporter involved in the importation of chloride into neurons or an activator of a transporter involved in the outflow of chloride from neurons.

In one embodiment, said inhibitor is an inhibitor of the expression of a transporter involved in the importation of chloride into neurons, preferably is siRNAs, shRNAs, antisense oligonucleotide, ribozymes or aptamers of a chloride transporter involved in the importation of chloride into neurons.

In another embodiment, said inhibitor is an inhibitor of the activity of a transporter involved in the importation of chloride into neurons. In one embodiment, said transporter involved in the importation of chloride into neurons is NKCC, preferably NKCC1.

In one embodiment, the inhibitor of NKCC is selected from the group comprising bumetanide, furosemide, ethacrynic acid, torsemide, azosemide, muzolimine, piretanide, tripamide and the like; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; analogs, functional derivatives and/or prodrugs thereof.

In another embodiment, said activator is an activator of the expression of the activity of a transporter involved in the outflow of chloride from neurons. In one embodiment, said transporter involved in the outflow of chloride from neurons is KCC, preferably KCC2.

In one embodiment, the effective amount ranges from about 0.01 mg to about 500 mg.

In one embodiment, the composition is administered to the subject in need thereof by subcutaneous, intramuscular, intravenous, intraocular, transdermal, topical, parenteral, intranasal and oral administration, or injection.

In one embodiment, the subject presents a number of CGG repeats in the 5'-UTR of FMR1 of at least 55, preferably of at least 200. In another embodiment, the subject is diagnosed with Fragile X syndrome. In still another embodiment, the subject is at risk of developing Fragile X syndrome. In one embodiment, the subject is a fetus and the composition is administered to his/her mother.

Definitions

In the present invention, the following terms have the following meanings:

"Fragile X syndrome" refers to a genetic disease associated with and/or caused by to a defect of the expression of the FMR1 gene and/or of the activity of the FMR1-encoded protein, FMRP.

In one embodiment, Fragile X syndrome refers to a condition wherein the FMR1 gene comprises at least 55 CGG repeats in the 5'-UTR. Preferably, FXS refers to a condition wherein the FMR1 gene comprises at least 200 CGG repeats in the 5'-UTR.

The expansion repeat in the 5'-UTR of FMR1 causes abnormal expression of the FMR1 gene, and consequently, abnormal function of the FMRP protein. Therefore, the skilled artisan will appreciate that Fragile X syndrome may also refer to a condition caused by and/or associated with one or more of the following: (1) a mutation in FMR1; (2) defective FMR1 expression; (3) increased and/or decreased expression of FMRP; (4) defective FMRP function; (5) increased and/or decreased expression of FMRP's natural binding partners; (6) an increased and/or decreased ability of FMRP to bind to its natural binding partners; (7) decreased or absent arginine methylation of FMRP; (8) increased methylation of FMR1 CpG repeats in the 5' UTR of exon 1; (9) the mislocalization or misexpression of FMRP within the cell (preferably in the neuron) or within the organism; and the like.

"Treatment" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject is successfully "treated" for Fragile X syndrome if, after receiving an effective amount of a modulator according to the present invention, the subject shows observable and/or measurable reduction in or absence of one or more of the following: reduction in one or more of the symptoms associated with the Fragile X Syndrome; and improvement in quality of life issues. The above parameters for assessing successful treatment and improvement in the disease are readily measurable by routine procedures familiar to a physician.

"Effective amount" refers to the level or amount of agent that is aimed at, without causing significant negative or adverse side effects to the target, (1) delaying or preventing the onset of Fragile X syndrome; (2) slowing down or stopping the progression, aggravation, or deterioration of one or more symptoms of Fragile X syndrome; (3) bringing about ameliorations of the symptoms of Fragile X syndrome; (4) reducing the severity or incidence of Fragile X syndrome; or (5) curing Fragile X syndrome. An effective amount may be administered prior to the onset of Fragile X syndrome, for a prophylactic or preventive action. Alternatively or additionally, the effective amount may be administered after initiation of Fragile X syndrome, for a therapeutic action.

"Subject" refers to a mammal, preferably a human. In one embodiment of the invention, the subject is a male. In another embodiment of the invention, the subject is a female.

In one embodiment, the term "healthy subject" refers to a subject not diagnosed with Fragile X syndrome. In another embodiment, a healthy subject does not present symptoms and/or clinical signs of Fragile X syndrome, wherein clinical signs of Fragile X syndromes include, but are not limited to, mild dysmorphic features, macrocephaly with long face, prominent ears, arched palate, thin face, joint hypermobility, fat feet and macroorchidism. In another embodiment, a healthy subject comprises a FMR1 gene with a number of CGG repeats in the 5'-UTR ranging from 5 to 54. In another embodiment, a healthy subject comprises a FMR1 gene with a number of CGG repeats in the 5'-UTR ranging from 55 to 200.

"Modulator" refers to a compound that modulates intracellular chloride level. Preferably, a modulator is a compound whose administration leads to a decrease of intracellular chloride concentration. In one embodiment, said modulator acts on the gene and/or protein expression and/or on the activity of a chloride transporter.

"Selective modulator" refers to a selective inhibitor and a selective activator.

"Inhibitor" refers to refers to a natural or synthetic compound that has a biological effect to inhibit or significantly reduce or down-regulate the expression of a gene and/or a protein or that has a biological effect to inhibit or significantly reduce the biological activity of a protein. Consequently, "a NKCC inhibitor" refers to a natural or synthetic compound that has a biological effect to inhibit or significantly reduce or down-regulate the expression of the gene encoding for NKCC and/or the expression of the NKCC protein and/or the biological activity of NKCC.

"Selective inhibitor" refers to that the affinity of the inhibitor for the chloride transporter for instance NKCC is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters in particular KCC2.

"Activator" refers to a natural or synthetic compound which binds to the protein and stimulates the expression of a gene and/or a protein or that has a biological effect to stimulate the biological activity of a protein. Consequently, "a KCC activator" refers to a natural or synthetic compound that has a biological effect to stimulate the expression of the gene encoding for KCC and/or the expression of the KCC protein and/or the biological activity of KCC. The activator usually mimics the action of a natural activator that binds to the transcription factor.

"Selective activator" refers to that the affinity of the activator for the chloride transporter for instance KCC2 is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters such as NKCC1.

"About": preceding a figure means plus or less 10% of the value of said figure.

"Analog" refers broadly to the modification or substitution of one or more chemical moieties on a parent compound and may include functional derivatives, positional isomers, tautomers, zwitterions, enantiomers, diastereomers, racemates, isosteres or stereochemical mixtures thereof.

"Functional derivative" refers to a compound which possesses the capacity to modulate the concentration of chloride into neurons (inhibits the importation or activates the outflow of chloride).

DETAILED DESCRIPTION

This invention relates to a composition comprising a modulator of intracellular chloride concentration for treating Fragile X syndrome.

In one embodiment of the invention, the modulator of intracellular chloride concentration is a modulator of a chloride transporter.

In one embodiment of the invention, the modulator of intracellular chloride concentration is a selective modulator of a chloride transporter.

In one embodiment, the modulator of a chloride transporter inhibits the importation of chloride into neurons, preferably through the inhibition of transporters involved in the importation of chloride into neurons.

In another embodiment, the selective modulator of a chloride transporter inhibits the importation of chloride into neurons, preferably through the inhibition of transporters involved in the importation of chloride into neurons.

In one embodiment of the invention, said modulator is an inhibitor of the chloride transporter involved in the importation of chloride into neurons.

In another embodiment of the invention, said modulator is a selective inhibitor of the chloride transporter involved in the importation of chloride into neurons.

In one embodiment of the invention, said modulator is an inhibitor of the protein and/or gene expression of a transporter involved in the importation of chloride into neurons.

In another embodiment of the invention, said modulator is a selective inhibitor of the protein and/or gene expression of a transporter involved in the importation of chloride into neurons.

Examples of transporters involved in the importation of chloride into neurons include, but are not limited to, NKCC (wherein NKCC stands for "Na—K-2Cl co-transporter"), such as, for example, NKCC1. In one embodiment, the modulator of a chloride transporter is thus an inhibitor of NKCC, preferably of NKCC1. In another embodiment, the modulator of a chloride transporter is a selective inhibitor of NKCC, preferably of NKCC1.

In one embodiment of the invention, the inhibitor of a chloride transporter inhibits the expression of said chloride transporter. Examples of inhibitors of the expression of a chloride transporter include, but are not limited to, siRNAs, shRNAs, antisense oligonucleotide, ribozymes or aptamers of a chloride transporter.

In another embodiment of the invention, the selective inhibitor of a chloride transporter is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then after raising aptamers directed against the chloride transporter as above described, the skilled man in the art can easily select those blocking chloride importation.

Inhibitors of chloride transporter gene expression for use in the present invention may be based on anti-sense oligonucleotide constructs. Anti-sense oligonucleotides, including anti-sense RNA molecules and anti-sense DNA molecules, would act to directly block the translation of chloride transporter mRNA by binding thereto and thus preventing protein translation or increasing mRNA degradation, thus decreasing the level of chloride transporter, and thus activity, in a cell. For example, antisense oligonucleotides of at least about 15 bases and complementary to unique regions of the mRNA transcript sequence encoding chloride transporter can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of chloride transporter gene expression for use in the present invention. chloride transporter gene expression can be reduced by contacting a subject or cell with a small double stranded RNA (dsRNA), or a vector or construct causing the production of a small double stranded RNA, such that chloride transporter gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of chloride transporter gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of chloride transporter mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of chloride transporter gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing Histamine H4 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In another embodiment, the inhibitor of a chloride transporter inhibits the activity of the chloride transporter. Examples of such inhibitors include, but are not limited to, small molecules, antibodies, minibodies, diabodies or fragments thereof binding to the chloride transporter, and antagonists of the chloride transporter.

In another embodiment, the inhibitor of the invention is an antibody (the term including antibody fragment) that can block the activity of a transporter involved in the importation of chloride into neurons.

In particular, the inhibitor of the invention may consist in an antibody directed against a transporter involved in the importation of chloride into neurons.

Antibodies directed against said transporter can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against said transporter can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g. U.S. Pat. No. 4,946,778) can be adapted to produce anti-modulator, or anti-modulator ligands single chain antibodies. Chloride transporter inhibitor useful in practicing the present invention also include anti-modulator, or anti-modulator ligands antibody fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed to allow rapid identification of fragments having the desired specificity to said transporter.

In another embodiment, the inhibitor of the invention can include isomers, tautomers, zwitterions, enantiomers, diastereomers, racemates, or stereochemical mixtures thereof. Inhibitors of the present invention can also comprise isosteres.

The term "isosteres" as used herein broadly refers to elements, functional groups, substituents, molecules, or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Other physical properties that isosteric compounds usually share include boiling point, density, viscosity, and thermal conductivity. However, certain properties are usually different: dipolar moments, polarity, polarization, size, and shape since the external orbitals may be hybridized differently.

The term "isomers" as used herein refers broadly to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure can exist in some of the compounds of the present invention, which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. Such compounds can also be prepared or isolated as pure stereoisomers, i.e., as individual enantiomers or diastereomers, or as stereoisomer-enriched mixtures. Tautomers are readily inter-convertible constitutional isomers and there is a change in connectivity of a ligand, as in the keto and enol forms of ethyl acetoacetate (including tautomers of any said compounds.) Zwitterions are inner salts or dipolar compounds possessing acidic and basic groups in the same molecule. At neutral pH, the cation and anion of most zwitterions are equally ionized.

Examples of such inhibitors include, but are not limited to, NKCC inhibitors, such as, for example, NKCC antagonists. In one embodiment, the modulator is an antagonist of NKCC1. In one embodiment, said inhibitor is a selective NKCC inhibitor, preferably a selective NKCC1 inhibitor.

In one embodiment of the invention, said selective inhibitor interacts directly with the chloride transporter.

In one embodiment, said selective inhibitor is an antagonist of a chloride transporter importing chloride into neurons.

In one embodiment of the invention, the inhibitor of a chloride transporter is an inhibitor of NKCC1, such as, for example, a diuretic (such as, for example, a loop diuretic); or a NKKC1 antagonist.

In one embodiment of the invention, the selective inhibitor decreasing the gene and/or protein expression and/or activity of the chloride co-transporter NKCC1, has a low affinity for KCC2.

In one embodiment of the invention, the selective inhibitor of the chloride transporter has an affinity for KCC2 inferior than $10^{-7}$ M, preferably $10^{-6}$ M, more preferably less than $10^{-5}$ M.

In another embodiment of the invention, the selective inhibitor of the chloride transporter has an affinity at least much higher to NKCC1 than to KCC2 (of at least 2 orders of magnitude, preferably of at least 4 orders of magnitude, more preferably of at least 5 orders of magnitude and most preferably of at least 6 orders of magnitude higher binding constant (at least $10^{-9}$, preferably more than $10^{-10}$).

In another embodiment of the invention, the selective inhibitor of the chloride transporter does not bind to KCC2 at all.

In one embodiment of the invention, the selective inhibitor of the chloride transporter refers to a molecule that has an affinity for the NKCC1 at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than its affinity for any one of other isoforms of NKCC transporters comprising NKCC2, KCC transporters comprising KCC1, KCC2, KCC3, KCC4, other transporter chloride including in a non-limiting list: $Cl^-HCO3^-$ transporter.

Examples of inhibitors of a chloride transporter, preferably of NKCC1, include, but are not limited to, bumetanide, furosemide, ethacrynic acid, torsemide, azosemide, muzolimine, piretanide, tripamide and analogs, functional derivatives and prodrugs of such compounds; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs, functional derivatives and prodrugs of such compounds.

Examples of analogs of bumetanide include, but are not limited to: bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)$_{n-1}$-ethyl ester, bumetanide benzyltrimethyl-ammonium salt, bumetanide cetyltrimethylammonium salt, pivaloyloxymethyl ester of bumetanide, methyl ester of bumetanide, N,N-dimethylaminoethyl ester of bumetanide, bumetanide [—(C═O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl)thioester, bumetanide S-[3-(dimethylaminopropyl)]thioester, bumetanide S—(N,N-diethylglycolamido)thioester, bumetanide S—(N,N-dimethylglycolamido)thioester, bumetanide S-pivaxetil thioester, bumetanide S-propaxetil thioester, bumetanide S-(methoxyipolyethyleneoxy)$_{n-1}$-ethyl]thioester, bumetanide [—(C=O)-S⁻] benzyltrimethyl-ammonium thioacid salt and bumetanide [—(C=O)—S] cetyltrimethylammonium thioacid salt; metast-able bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl)thioester, bumetanide O-[3-(dimethylaminopropyl)]thioester, bumetanide O—(N,N-diethylglycolamido)thioester, bumetanide O-pivaxetil thioester, bumetanide O-propaxetil thioester, bumetanide O-[methoxy(poryethyleneoxy)$_{n-1}$ ethyl]thioester, bumetanide [—(C=S)—O⁻] benzyltrimemyl-ammonium thioacid salt and bumetanide [—(C=S)—O⁻] cetyltrimethylammonium thioacid salt.

Examples of analogs of furosemide include, but are not limited to: furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)$_{n-1}$-ethyl ester, furosemide pivaxetil ester, furosemide propaxetil ester, furosemide benzyltrimethylammonium acid salt and furosemide cetyltrimethylammonium acid salt, furosemide [—(C=O)-SH] thioacid, furosemide S-methyl thioester, furosemide S-cyanomethyl thioester, furosemide S-ethyl thioester, furosemide S-isoamyl thioester, furosemide S-octyl thioester, furosemide S-benzyl thioester, furosemide S-(morpholinoethyl)thioester, furosemide S-[3-(dimethylaminopropyl)]thioester, furosemide S—(N,N-diethylglycolamido)thioester, furosemide S—(N,N-dimethylglycolamido)thioester, furosemide S-pivaxetil thioester, furosemide S-propaxetil thioester, furosemide S-[methoxy(polyethyleneoxy)$_{n-1}$-ethyl]thioester, furosemide [—(C=O)—S⁻] benzyltrimethylammonium thioacid salt and furosemide [—(C=O)—S⁻] cetyltrimethylammonium thioacid salt, metasta-stable furosemide [—(C=S)—OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl)thioester, furosemide O-[3-(dimethylaminopropyl)]thioester, furosemide O—(N,N-diethylglycolamido)thioester, furosemide O—(N,N-dimethylglycolamido)thioester, furosemide O-pivaxetil thioester, furosemide O-propaxetil thioester, furosemide O-[methoxy(polyethyleneoxy)$_{n-1}$-ethyl]thioester, furosemide [—(C=S)—O⁻]benzyltrimethyl-ammonium thioacid salt and furosemide [—(C=S)—O⁻] cetyltrimethylammonium thioacid salt; furosemide thioaldehyde, furosemide [—(C=S)—SH] dithioacid, furosemide methyl dithioester, furosemide cyanomethyl dithioester, furosemide ethyl dithioester, furosemide isoamyl di-thioester, furosemide octyl dithioester, furosemide benzyl dithioester, furosemide dibenzyl-thioamide, furosemide diethylthioamide, furosemide morpholinoethyl dithioester, furosemide 3-(dimethylaminopropyl) dithioester, furosemide N,N-diethylglycolamido dithioester, furosemide N,N-dimethylglycolamido dithioester, furosemide pivaxetil dithioester, furosemide propaxetil dithioester, furosemide methoxy(polyethyleneoxy)$_{n-1}$ ethyl dithioester, furosemide benzyltrimethylammonium dithioacid salt and furosemide cetyltrimethylammonium dithioacid salt.

Examples of analogs of piretanide include, but are not limited to: piretanide aldehyde, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzyltrimethylammonium salt, piretanide cetyltrimethylammonium salt, piretanide N,N-dimethylglycolamide ester, piretanide methoxy(polyethyleneoxy)$_{n-1}$-ethyl ester, piretanide pivaxetil ester, piretanide propaxetil ester, piretanide [—(C=O)—SH] thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl)thioester, piretanide S-[3-(dimethylaminopropyl)]thioester, piretanide S—(N,N-diethylglycolamido)thioester, piretanide S—(N,N-dimethylglycolamido)thioester, piretanide S-pivaxetil thioester, piretanide S-propaxetil thioester, piretanide S-[methoxy(polyethyleneoxy)$_{n-1}$ ethyl]thioester, piretanide [—(C=O)—S⁻] benzyltrimethylammonium thioacid salt and piretanide [—(C=O)—S⁻] cetyltrimethylammonium thioacid salt; metastable piretanide [—(C=S)—OH] thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl)thioester, piretanide O-[3-(dimethylaminopropyl)]thioester, piretanide O—(N,N-diethylglycolamido)thioester, piretanide, O—(N,N-dimethylglycolamido)thioester, piretanide O-pivaxetil thioester, piretanide O-propaxetil thioester, piretanide O-[methoxy (polyethyleneoxy)$_{n-1}$ ethyl]thioester, piretanide [—(C=S)—O⁻] benzyltrimethylammonium thioacid salt and piretanide [—(C=S)—O⁻] cetyltrimethylammonium thioacid salt; piretanide thioaldehyde, piretanide [—(C=S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethyl-thioamide, piretanide morpholinoethyl dithioester, piretanide 3-(dimethylaminopropyl) di-thioester, piretanide N,N-diethylglycolamido dithioester, piretanide N,N-dimethylglycolamido dithioester, piretanide pivaxetil dithioester, piretanide propaxetil dithioester, piretanide methoxytpolyethyleneoxyLrethyl dithioester, piretanide benzyl-trimethylammonium dithioacid salt and piretanide cetyltrimethylammonium dithioacid salt.

Examples analogs of azozemide and include, but are not limited to: tetrazolyl-substituted azosemides (such as methoxymethyl tetrazolyl-substituted azosemides, methylthiomethyl tetrazolyl-substituted azosemides, N-mPEG350-tetrazolyl-substituted azosemides), azosemide benzyltrimethylammonium salt, azosemide cetyltrimethylammonium salt, pyridine-substituted torsemide quaternary ammonium salts or the corresponding inner salts (zwitterions), methoxymethyl pyridinium torsemide salts, methylthioethyl pyridinium torsemide salts and N-mPEG350-pyridinium torsemide salts.

In another embodiment, an analog of an inhibitor according to the invention may have a formula as described in the patent application WO2006110187. Examples of said analogs include, but are not limited to, compounds of general formula I, II and/or III:

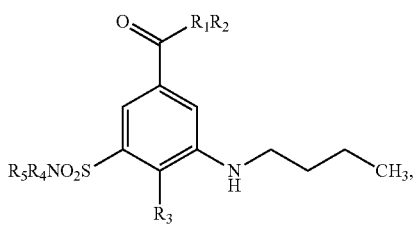

(I)

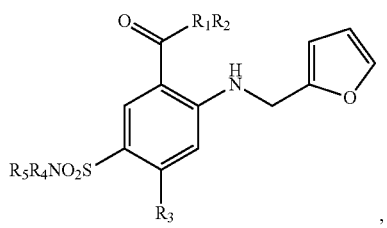

(II)

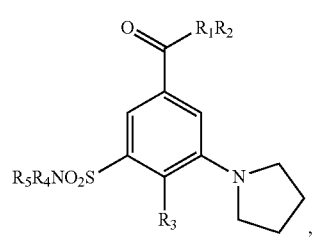

(III)

or a pharmaceutically acceptable salt, solvate, tautomer or hydrate thereof, wherein
R1 is not present, H or O;
R2 is H or when R1 is O, is selected from the group consisting of: alkylaminodialkyl, alkylaminocarbonyldialkyl, alkyloxycarbonylalkyl, alkylaldehyde, alkylketoalkyl, alkylamide, an alkylammonium group, alkylcarboxylic acid, alkylheteroaryls, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkylalkyl and methylthioalkaryl, unsubstituted or substituted, and when R1 is not present, R2 is selected from the group consisting of: hydrogen, dialkylamino, diarylamino, dialkylaminodialkyl, dialkylcarbonylaminodialkyl, dialkylesteralkyl, dialkylaldehyde, dialkylketoalkyl, dialkylamido, dialkylcarboxylic acid, and dialkylheteroaryls, unsubstituted or substituted;
R3 is selected from the group consisting of: aryl, halo, hydroxy, alkoxy, and aryloxy, unsubstituted or substituted; and
R4 and R5 are each independently selected from the group consisting of: hydrogen, alkylaminodialkyl, alkylhydroxyaminodialkyl, unsubstituted or substituted.

Another non-limiting example of said analogs of an inhibitor of the invention is a compound of general formula IV

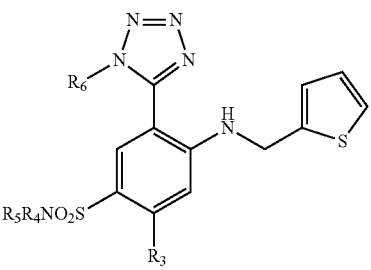

(IV)

or a pharmaceutically acceptable salt, solvate, tautomer or hydrate thereof, wherein
R3, R4 and R5 are as defined above; and
R6 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted.

Another non-limiting example of said analogs is a compound of general formula V (V)

or a pharmaceutically acceptable salt, solvate, tautomer or hydrate thereof, wherein R7 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted; and X⁻ is a halide such as bromide, chloride, fluoride, iodide or an anionic moiety such as mesylate or tosylate; alternatively, X⁻ is not present and the compound forms an "inner" or zwitterionic salt by loss of a proton from the sulfonylurea moiety (—SO2-NH—CO—).

The term "alkyl" as used herein refers to a straight or branched chain saturated or partially unsaturated hydrocarbon radical, wherein by "unsaturated" is meant the presence of 1, 2 or 3 double or triple bonds, or a combination thereof. Examples of alkyl groups include, but are not limited to, methyl, ethyl, isopropyl, tert-butyl, n-pentyl and the like.

The term "alkylene" as used herein refers to a straight or branched chain having two terminal monovalent radical centers derived by the removal of one hydrogen atom from each of the two terminal carbon atoms of straight-chain parent alkane.

The term "aryl" as used herein refers to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

The term "halo" as used herein refers to bromo, chloro, fluoro or iodo. Alternatively, the term "halide" as used herein refers to bromide, chloride, fluoride or iodide.

The term "hydroxyl" as used herein refers to the group —OH.

The term "alkoxy" as used herein alone or as part of another group, refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like.

The term "aryloxy" as used herein refers to the group —ArO wherein Ar is aryl or heteroaryl. Examples include, but are not limited to, phenoxy, benzyloxy and 2-naphthyloxy.

The term "amino" as used herein refers to —NH$_2$ in which one or both of the hydrogen atoms may optionally be replaced by alkyl or aryl or one of each, optionally substituted.

The term "alkylthio" as used herein alone or as part of another group, refers to an alkyl group, as defined herein, appended to the parent molecular moiety through a sulfur moiety. Representative examples of alkylthio include, but are not limited to, methylthio, ethylthio, n-propylthio, isopropylthio, n-butylthio, and the like.

The term "carboxy" as used herein refers to the group —CO$_2$H.

The term "quaternary ammonium" as used herein refers to a chemical structure having four bonds to the nitrogen with a positive charge on the nitrogen in the "onium" state, i.e., "R$_4$N$^+$" or "quaternary nitrogen", wherein R is an organic substituent such as alkyl or aryl. The term "quaternary ammonium salt" as used herein refers to the association of the quaternary ammonium with a cation.

The term "substituted" as used herein refers to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulf[iota]nyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, ureido and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent.

The term "solvate" as used herein is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, isopropanol, ethanol, methanol, DMSO, ethyl acetate, acetic acid, or ethanolamine.

The term "hydrate" as used herein refers to the compound when the solvent is water.

In another embodiment, an analog of an inhibitor of the chloride transporter according to the invention may have a formula as described in the patent application WO2012/018635. Examples of said analogs include but are not limited to a compound of formula:

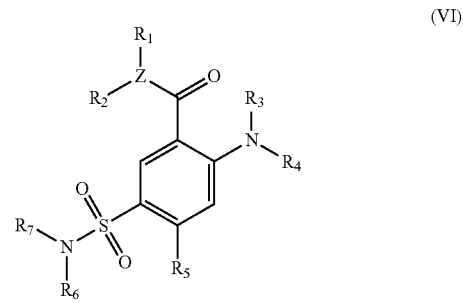

(VI)

or a pharmaceutically acceptable salt thereof, wherein:
Z is oxygen or nitrogen;
R1 and R2 are each independently hydrogen, alkyl, aryl, arylalkyl, heteroaryl, heteroaryl alkyl, heterocyclo alkyl, or R1 and R2, together with the atom to which they are attached, form a 4-7 membered heterocyclic ring that can have one or more additional heteroatoms and can have one or more substituents, with the proviso that if Z is oxygen, then R2 is not present;
R3 and R4 are each independently hydrogen, alkyl, cycloalkyl, cycloalkyl alkyl, aryl, arylalkyl, heteroaryl, or heteroarylalky, or R3 and R4, together with the atom' to which they are attached, form a 4-7 membered heterocyclic ring that can have one or more additional heteroatoms and can have one or more substituents;
R5 is halo, aryl, aryloxy, arylamino, heteroarylamino, heterocycloalkyl, heteroaryl, heteroaryloxy, heterocycloalkoxy, or alkythio; and
R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents.

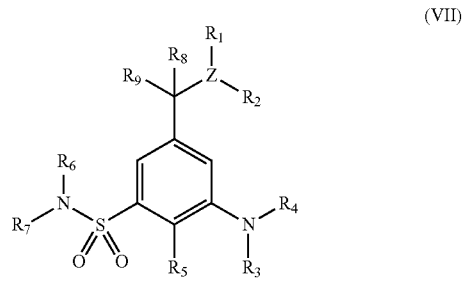

(VII)

or a pharmaceutically acceptable salt thereof, wherein:
Z is oxygen or nitrogen;

R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;

R5 is alkoxy, halo, aryl, aryloxy, alkaryloxy, arylamino, heteroarylamino, heterocycloalkyl, heteroaryl, heteroryloxy, heterocycloalkoxy, or alkythio;

R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and R8 and R9 are each independently hydrogen, alkyl, or R8 and R9 together with the atom to which they are attached, form a 3-6 membered substituted or unsubstituted cycloalkyl or heterocycloalkyl ring.

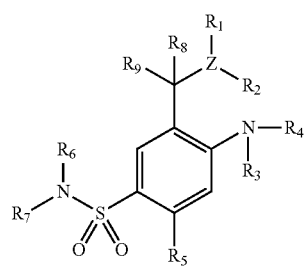

(VIII)

or a pharmaceutically acceptable salt thereof, wherein:
Z is oxygen or nitrogen;
R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;

R5 is alkoxy, halo, aryl, aryloxy, alkaryloxy, arylamino, heteroarylamino, heterocycloalkyl, heteroaryl, heteroaryloxy, heterocycloalkoxy, or alkythio;

R6 and R7 are each independently hydrogen, acyl, alkyl, cycloalkyl alky], aryl or arylalkyl, or R6 and R7, together with the atom to which they are attached, form a 4-7 membered heterocyclic ring that can have one or more additional heteroatoms and can have one or more substituents; and R8 and R9 are each independently hydrogen, alkyl, or R8 and R9 together with the atom to which they are attached, form a 3-6 membered substituted or unsubstituted cycloalkyl or heterocycloalkyl ring.

In another embodiment, an analog of the inhibitor of the chloride transporter may have a formula as described in the patent applications incorporated herein US2007/0155729, GB2207129, in U.S. Pat. Nos. 4,247,550; 3,985,777; 7,282,519.

In another embodiment, an alternative inhibitor of NKCC activity is selected from the group comprising non-diuretic compounds: protein kinase inhibitors staurosporine and K252a, through SPAK autophosphorylation and substrate phosphorylation of the co-transporter, or the sulfhydryl agents N-ethylmaleimide (NEM) and diamide (Gagnon et al. 2006 Mol. Cell. Biol. 26(2):689-698).

In another embodiment of the invention, the modulator of chloride intracellular level is oxytocin. Oxytocin has been shown to act by reducing intracellular chloride and therefore to act similarly to NKCC1 antagonists.

In another embodiment of the invention, the modulator of chloride intracellular level is not oxytocin.

In another embodiment of the invention, the modulator of chloride intracellular level is not valproic acid.

In another embodiment of the invention, the modulator of chloride intracellular level is not bendroflumethiazide, benzthiazide, buthiazide, chlorothiazide, cyclothiazide, epithiazide, metalthiazide, hydrochlorothiazide, hydro-flumethiazide, methylclothiazide, polythiazide, trichlormethiazide, chlorthalidone, indapamide, metolazone and quinethazone.

Preferably, the modulator of the intracellular chloride level is bumetanide, analogs, functional derivatives and prodrugs thereof.

Another object of the present invention is a modulator of a chloride transporter that improves the outflow of chloride from neurons, preferably through the activation of transporters involved in the outflow of chloride from neurons.

In one embodiment of the invention, the modulator of a chloride transporter improves the outflow of chloride from neurons, preferably through the activation of transporters involved in the outflow of chloride from neurons.

In another embodiment of the invention, said modulator is a modulator of a chloride transporter that improves the outflow of chloride from neurons, preferably through the activation of transporters involved in the outflow of chloride from neurons.

In another embodiment of the invention, said modulator is an activator of a chloride transporter involved in the outflow of chloride from neurons.

In another embodiment of the invention, said modulator is a selective activator of a chloride transporter involved in the outflow of chloride from neurons.

Examples of transporters involved in the outflow of chloride from neurons include, but are not limited to, KCC (wherein KCC stands for "K—Cl co-transporter"), such as, for example, KCC2. In one embodiment, said modulator of a chloride transporter is thus a selective activator of KCC, preferably of KCC2.

Examples of KCC2 activators include but are not limited to: N-ethylmaleimide (NEM), the chloride channel inhibitor 5-nitro-2-(3-phenylpropylamino)benzoic acid (NPPB), CLP257, CLP290 and analogs, functional derivatives and prodrugs thereof.

Examples of KCC2 activators are described in the international patent applications incorporated herein: WO2009/114950; WO2009/097695; WO2010132999.

In one embodiment of the invention, the modulator improves the expression of a chloride transporter, or improves its presence on the cell surface.

In another embodiment, the selective modulator of KCC improves the expression of a chloride transporter, or improves its presence on the cell surface.

In another embodiment, the activator of KCC improves the expression of a chloride transporter, or improves its presence on the cell surface.

In another embodiment, the selective activator of KCC improves the expression of a chloride transporter, or improves its presence on the cell surface.

In one embodiment of the invention, the modulator of the chloride transporter is involved in the outflow of chloride from neurons.

In another embodiment of the invention, the selective modulator of the chloride transporter is involved in the outflow of chloride from neurons.

In another embodiment of the invention, the activator of the chloride transporter increases the outflow of chloride from neurons.

In another embodiment of the invention, the selective activator of the chloride transporter increases the outflow of chloride from neurons.

In another embodiment, the modulator improves the activity of a chloride transporter, for example is an agonist of a chloride transporter or an antibody or a fragment thereof which activates the chloride transporter.

Examples of such modulators include, but are not limited to, activators of KCC, such as, for example, KCC agonists. In one embodiment, the modulator is an agonist of KCC2.

In one embodiment of the invention, the composition comprises an effective amount of a modulator of intracellular chloride concentration.

According to the invention, the effective amount of a modulator of intracellular chloride concentration is calculated in order to reach a desired intracellular concentration of chloride.

Indeed, the Applicant surprisingly showed that the intracellular concentration of chloride is more elevated in Fragile X syndrome rodents than in naïve ones (see Examples).

Therefore, according to an embodiment, the effective amount of a modulator of intracellular chloride concentration corresponds to the amount to be administered to a subject in need thereof for reaching the intracellular chloride concentration measured in a healthy subject. Preferably, said healthy subject shares characteristics with the Fragile X syndrome subject to be treated, such as, for example, the same age, sex, diet, weight and the like. More preferably, said healthy subject presents a number of repeats with in the 5'-UTR of the FMR1 gene ranging from 5 to 54.

In one embodiment of the invention, the effective amount of a modulator ranges from about 0.01 mg to about 500 mg, preferably from about 0.05 mg to about 100 mg, more preferably from about 0.1 mg to about 10 mg and even more preferably from about 0.5 mg to about 1.5 mg.

According to one embodiment of the invention, the composition of the invention is for treating behavioral and/or cognitive symptoms associated with Fragile X syndrome. In one embodiment, the administration to a subject in need thereof of the composition of the invention results in the alleviation of behavioral symptoms of Fragile X syndrome.

Examples of behavioral and/or cognitive symptoms of Fragile X syndrome include, but are not limited to, hyperactivity, stereotypy, anxiety, seizure, impaired social behavior, cognitive delay, hypersensitivity to sensory stimuli, mood disorders, disrupt sleep patterns, irritability, aggression or self-injurious behavior, mental retardation, learning disabilities (such as, for example, delays in learning how to sit, walk and talk), nervous or cluttered speech, difficulty with face encoding and deficient central executive, working, phonological and/or visual-spatial memories.

In one embodiment of the invention, the behavioral and/or cognitive symptom associated with Fragile X syndrome is not an autistic symptom or a symptom associated with an autism spectrum disorder.

Methods for assessing the efficacy of the treatment are readily measurable by routing procedures familiar to a physician, such as, for example, use of scales. Examples of scales that may be used for assessing the efficacy of the treatment of Fragile X syndrome include, but are not limited to, the ABC scale, the GRAM scale and the CGI scale.

According to one embodiment of the invention, the composition of the invention is for alleviating the occurrence of ocular symptoms and/or othorhinolaryngo local manifestations associated with Fragile X syndromes. In one embodiment, the administration to a subject in need thereof of the composition of the invention results in the alleviation of ocular symptoms and othorhinolaryngo local manifestations and/or in the reduction of the occurrence of said symptoms, such as, for example, in the reduction of the occurrence of ophthalmologic problems including strabismus, otitis media and sinusitis.

According to one embodiment of the invention, the composition of the invention is for treating synaptic defects/symptoms associated with Fragile X syndromes. In one embodiment, the administration to a subject in need thereof of the composition of the invention results in the alleviation of synaptic defects associated with Fragile X syndrome.

Examples of synaptic defects/symptoms associated with Fragile X syndrome include, but are not limited to, defective synaptic morphology (such as, for example, an abnormal number, length, and/or width of dendritic spines) and defective synaptic function (such as, for example, enhanced long-term depression (LTD) and/or reduced long-term potentiation (LTP)).

In one embodiment of the invention, the subject to be treated presents a number of CGG repeats in the 5'-UTR of FMR1 of at least 55, preferably of at least 200.

In one embodiment of the invention, the subject to be treated is diagnosed with Fragile X syndrome; preferably he/she presents a number of CGG repeats in the 5'-UTR of FMR1 of at least 200. In one embodiment, the diagnosed subject already presents symptoms of Fragile X syndrome. In another embodiment, the diagnosed subject is treated before the onset of Fragile X syndrome symptoms.

In another embodiment of the invention, the subject to be treated is at risk of developing Fragile X syndrome. In one embodiment of the invention, said risk corresponds to the presence in the kindred of Fragile X syndrome patients. In another embodiment of the invention, said risk correspond to the presence, in the FMR1 gene of at least one of the parents of the subject, of a number of CGG repeats in the 5'-UTR ranging from 55 to 200 or of more than 200.

In one embodiment of the invention, the subject to be treated is not an autistic patient. Preferably, said subject is not diagnosed with autism or another autism spectrum disorder.

The Applicant surprisingly showed that delivery was a key event in the development of Fragile X syndrome (see Examples). Therefore, in one embodiment, the composition of the invention is administered to a pregnant woman. According to the invention, the term "pregnant woman" refers to a woman from the conception date to the end of the delivery.

According to an embodiment, the composition is administered to a pregnant woman when her fetus has been prenatally diagnosed with Fragile X syndrome, preferably when the fetus presents a number of CGG repeats superior to 200. According to an embodiment, the composition is administered to a pregnant woman when her fetus presents a risk of developing Fragile X syndrome. In one embodiment of the invention, said risk corresponds to the presence in the kindred of Fragile X syndrome patients. In another embodiment of the invention, said risk correspond to the presence, in the FMR1 gene of at least one of the parents of the subject, of a number of CGG repeats in the 5'-UTR ranging from 55 to 200 or of more than 200.

In one embodiment of the invention, the composition is perinatally administered to a child. As used herein, the term "perinatally" refers to a few hours after birth, preferably 10, 8, 6, 5, 4, 3, 2 or 1 hour(s) after birth. Preferably, this embodiment applies when the child has been prenatally diagnosed with Fragile X syndrome, preferably when he/she presents a number of CGG repeats superior to 200. According to an embodiment, the composition may also be perinatally administered when the child presents a risk of developing Fragile X syndrome. In one embodiment of the invention, said risk corresponds to the presence in the kindred of Fragile X syndrome patients. In another embodiment of the invention, said risk correspond to the presence, in the FMR1 gene of at least one of the parents of the subject, of a number of CGG repeats in the 5'-UTR ranging from 55 to 200 or of more than 200.

In one embodiment of the invention, the subject is a young child. As used herein, the term "young child" refers to a child from 0 to 3 years old.

In another embodiment of the invention, the subject is a child. In one embodiment, the term "child" may refer to subjects aged from 0 to 12, preferably from 3 to 12. More generally, the term child refers to a subject which is not yet an adolescent.

In another embodiment of the invention, the subject is an adolescent. In one embodiment, the term "adolescent" may refer to subjects aged from about 12 to 17, but the skilled artisan will appreciate that the length of adolescence may vary from one individual to another.

In another embodiment, the subject is an adult. In one embodiment, the term "adult" may refer to subjects of more than 17 years old. More generally, the term adult refers to a subject which is no more an adolescent.

The present invention also relates to a pharmaceutical composition for treating Fragile X syndrome in a subject in need thereof, wherein said pharmaceutical composition comprises an effective amount of a modulator of intracellular chloride concentration and at least one pharmaceutically acceptable excipient.

As used herein the term "pharmaceutically acceptable excipient" refers to an excipient that does not produce an adverse, allergic or other untoward reaction when administered to an animal, preferably a human. It may include any and all solvents, dispersion media, coatings, antibacterial and antifungal agents, isotonic and absorption delaying agents and the like. For human administration, preparations should meet sterility, pyrogenicity, and general safety and purity standards as required by FDA Office of Biologics standards.

Another object of the invention is a medicament for treating Fragile X syndrome comprising an effective amount of a modulator of intracellular chloride concentration.

The composition, pharmaceutical composition or medicament of the invention may be administered by several routes of administration. Examples of adapted routes of administration include, but are not limited to, subcutaneous, intramuscular, intravenous, intraocular, transdermal, topical, parenteral, intranasal and oral administration, or injection. The type of form for administration will be matched to the severity of the syndrome as well as to the age, weight, sex, etc. . . . of the subject to be treated.

According to an embodiment, the composition, pharmaceutical composition or medicament of the invention is in a form adapted for injection, preferably selected from the group comprising solutions, such as, for example, isotonic solution, saline solution, sterile aqueous solutions, dispersions, emulsions, suspensions, solid forms suitable for using to prepare solutions or suspensions upon the addition of a liquid prior to use, such as, for example, powder, freeze-dried compositions, liposomal forms and the like.

According to an embodiment, the composition, pharmaceutical composition or medicament of the invention is in a form adapted to oral administration. According to a first embodiment, the form adapted to oral administration is a solid form selected from the group comprising tablets, pills, capsules, soft gelatin capsules, sugarcoated pills, orodispersing tablets, effervescent tablets or other solids. According to a second embodiment, the form adapted to oral administration is a liquid form, such as, for example, a drinkable solution, a buccal spray, liposomal forms and the like.

According to an embodiment, the composition, pharmaceutical composition or medicament of the invention is in a form adapted for local delivery via the nasal and respiratory routes. Examples of formulations suitable for nasal administration include but are not limited to, nasal solutions, sprays, aerosols and inhalants.

According to an embodiment, the composition, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

According to an embodiment, the composition, pharmaceutical composition or medicament of the invention is in the form of, or comprises, liposomes and/or nanoparticles.

According to an embodiment, the composition, pharmaceutical composition or medicament of the invention further comprises some excipients, such as, for example, surfactants (e.g. hydroxypropylcellulose); suitable carriers, such as, for example, solvents and dispersion media containing, for example, water, monosodium or disodium phosphate, sodium, potassium, calcium or magnesium chloride, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

In one embodiment of the invention, the composition, pharmaceutical composition or medicament of the invention may be used in conjunction with delivery systems that facilitate delivery of the agents to the central nervous system. For example, various blood brain bather (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

The present invention can also relate to a prodrug of the modulator of the intracellular chloride concentration within neurons or an encapsulation of said modulator.

In one embodiment, the composition, pharmaceutical composition or medicament of the invention is a prodrug of the selective modulator of intracellular chloride concentration within neurons.

In another embodiment, the composition, pharmaceutical composition or medicament of the invention is a prodrug of the inhibitor of chloride importation within neurons.

In another embodiment, the composition, pharmaceutical composition or medicament of the invention is a prodrug of the selective inhibitor of chloride importation within neurons.

In another embodiment, the composition, pharmaceutical composition or medicament of the invention is a prodrug of the activator of chloride outflow from neurons.

In another embodiment, the composition, pharmaceutical composition or medicament of the invention is a prodrug of the selective activator of chloride outflow from neurons.

Prodrugs as described herein are capable of passage across the blood-brain barrier and may undergo hydrolysis by CNS esterases to provide the active compound.

Prodrugs provided herein may also exhibit improved bioavailability, improved aqueous solubility, improved passive intestinal absorption, improved transporter-mediated intestinal absorption, protection against accelerated metabolism, tissue-selective delivery, less (or fewer) side effects, lessened or no deleterious drug interaction with other medications, and/or passive enrichment in the target tissue.

The term "prodrug" as used herein refers to a compound that is converted under physiological conditions, by solvolysis or metabolically to a specified compound that is pharmaceutically/pharmacologically active. The "prodrug" can be a compound of the present invention that has been chemically derivatized such that it retains some, all or none of the bioactivity of its parent drug compound and is metabolized in a subject to yield the parent drug compound. The prodrug of the present invention may also be a "partial prodrug" in that the compound has been chemically derivatized such that it retains some, all or none of the bioactivity of its parent drug compound and is metabolized in a subject to yield a biologically active derivative of the compound.

Prodrugs can be formed by attachment of biocompatible polymers, such as those previously described including polyethylene glycol (PEG), to compounds of the present invention using linkages degradable under physiological conditions. See also Schacht, et al. (1997) Poly(ethylene glycol) Chemistry and Biological Applications, American Chemical Society, San Francisco, Calif. 297-315. Attachment of PEG to proteins can be employed to reduce immunogenicity and/or extend the half-life of the compounds provided herein. Any conventional PEGylation method can be employed, provided that the PEGylated agent retains at least some pharmaceutical activity.

In one embodiment, the selective inhibitor of the invention is bumetanide-PEGylated.

In one embodiment, the present invention further provides prodrugs comprising the compounds described herein. The prodrugs can be formed utilizing a hydrolyzable coupling to the compounds described herein. Ettmayer, et al. (2004) J. Med. Chem. 47(10): 2394-2404; Testa and Mayer (2003) Hydrolysis in Drug and Prodrug Metabolism: Chemistry, Biochemistry and Enzymology Wiley-Verlag Helvetica Chimica Acta, Zuerich (Chapters 1-1): 1-780.

According to one embodiment of the invention, the composition, the pharmaceutical composition or the medicament of the invention is administered at least once a day, preferably twice a day, more preferably at least three times a day.

In one embodiment of the invention, the daily amount of a modulator to be administered to a subject ranges from about 0.01 mg/day to about 500 mg/day, preferably from about 0.05/day mg to about 100 mg/day, more preferably from about 0.1 mg/day to about 10 mg/day and even more preferably from about 0.5 mg/day to about 1.5 mg/day.

According to one embodiment of the invention, the administration dose of the pharmaceutical composition is determined by the skilled artisan and personally adapted to each subject.

In one embodiment of the invention, the modulator is administered in a sustained-release form. In one embodiment of the invention, the composition comprises a delivery system that controls the release of the modulator. Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, brasiliensis, polydienes, and halogenated natural and synthetic rubbers; and flexible thermoset resins such as polyurethanes, epoxy resins; biodegradable polymers and the like.

In another embodiment of the invention, the modulator of the present invention is administered in combination with other therapies that could include: speech therapy, behavioral therapy, sensory integration occupational therapy, special education, or individualized educational plans, and, when necessary, treatment of physical abnormalities.

Another object of the invention is a method for treating Fragile X syndrome in a subject in need thereof, wherein the method comprises administering to the subject an effective amount of a modulator of a chloride transporter. In one embodiment of the invention, said effective amount is calculated in order to reach a desired intracellular concentration of chloride.

In one embodiment of the invention, the method of treating comprises administering to the subject the composition, the pharmaceutical composition or the medicament of the invention.

In one embodiment of the invention, the method is for treating behavioral and/or cognitive symptoms of Fragile X syndrome.

In another embodiment of the invention, the method is for treating ocular symptoms and/or othorhinolaryngo local symptoms of Fragile X syndrome.

In another embodiment, the method of the invention is for treating synaptic symptoms/defects of Fragile X syndrome.

In one embodiment of the invention, the subject in need of a treatment presents a number of CGG repeats in the 5'-UTR of FMR1 of at least 55, preferably of at least 200. In one embodiment of the invention, the subject to be treated is diagnosed with Fragile X syndrome, and already presents or not symptoms of Fragile X syndrome. In another embodiment of the invention, the subject in need of a treatment is at risk of developing Fragile X syndrome.

The present invention also relates to a method for treating Fragile X syndrome in a fetus, and comprises administering to his/her mother an effective amount of a modulator of a chloride transporter.

In one embodiment of the invention, the subject is for perinatally treating a child.

In one embodiment of the invention, the subject is a young child, a child, an adolescent or an adult.

In one embodiment of the invention, the method of the invention comprises subcutaneously, intramuscularly, intravenously, intraocularly, transdermally, topically, parenterally, intranasally or orally administering the modulator of the invention, or its injection.

In one embodiment of the invention, the method of the invention comprises administering the modulator of the invention at least once a day, preferably twice a day, more preferably at least three times a day. In another embodiment of the invention, a daily amount of a modulator ranging from about 0.01 mg/day to about 500 mg/day, preferably from about 0.05/day mg to about 100 mg/day, more preferably from about 0.1 mg/day to about 10 mg/day and even more preferably from about 0.5 mg/day to about 1.5 mg/day is administered to the subject.

The present invention also relates to a method for decreasing the intracellular concentration of chloride in a Fragile X syndrome subject, preferably the neuronal intracellular concentration of chloride.

Another object of the invention is a method for modulating the intracellular chloride concentration of a subject, wherein the method comprises administering to the subject in need thereof an effective amount of a modulator of a chloride transporter.

The present invention also relates to a method for decreasing the driving force of GABA in a Fragile X syndrome subject.

In one embodiment of the invention, the method comprises administering to the subject an effective amount of a modulator of a chloride transporter.

In one embodiment of the invention, said effective amount is calculated in order to reach a desired intracellular concentration of chloride.

In one embodiment of the invention, the method comprises administering to the subject in need thereof the composition, the pharmaceutical composition or the medicament of the invention.

EXAMPLES

Figure 1C:
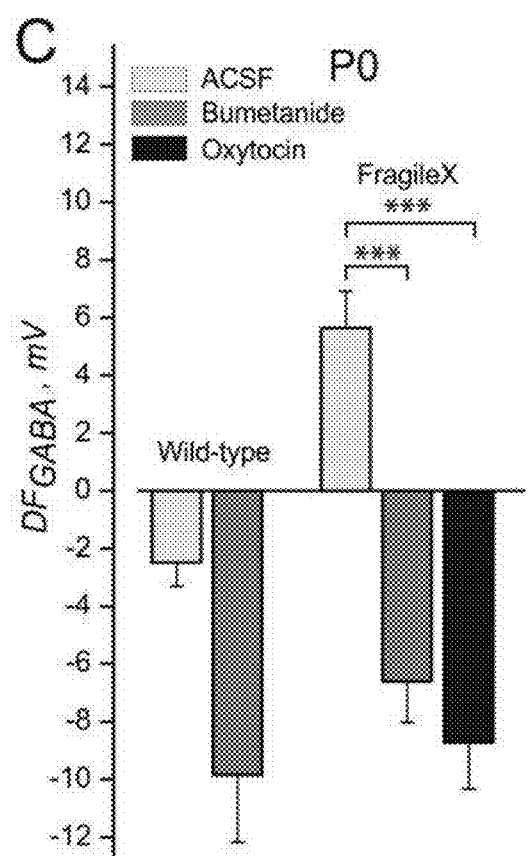
FIG. 1 is a combination of graphs showing a comparison of developmental profile of driving force for GABA ($DF_{GABA}$) in hippocampal slices from pre- and postnatal transgenic mouse model for the Fragile X syndrome versus wild type animals: A. Plot of $DF_{GABA}$ measured with single $GABA_A$ channels recordings (for details see Tyzio et al., 2006) from CA3 hippocampal pyramidal cells at prenatal (E20) and postnatal (P0, P7, P14 and P28-37) stages. Note that $DF_{GABA}$ is significantly more positive in Fragile X at ages P0, P14 and P28-37. Also there is no perinatal hyperpolarizing shift of $DF_{GABA}$ in Fragile X model (at P0 $p<0.005$, at p14 $p<0.05$, at P28-37 $p<0.005$); B. I-V relationships of the currents through $GABA_A$ channels at P0 in two CA3 pyramidal cells from Fragile X before and after application of bumetanide. Their reversal potential corresponds to $DF_{GABA}$; note the shift of reversal potential from depolarizing to hyperpolarizing. On the inset—examples of single $GABA_A$ channels openings at different holding potentials; C. Action of oxytocin and bumetanide on $DF_{GABA}$ in CA3 pyramidal cells from newborn (P0) Fragile X and wild type. In the wild type pyramidal cells $DF_{GABA}$ is initially hyperpolarizing at P0 as a result of maternal oxytocin action. Bumetanide application increases hyperpolarization. In slices from Fragile X mouse $DF_{GABA}$ is positive at P0 and both oxytocin and bumetanide shift it to hyperpolarization at P0 ($p<0.005$).

The present invention is further illustrated by the following examples.

Materials and Methods

Fragile X Knock Out Mice (FXS Mice)

Mice lacking Fmr1 (referred to as Fmr1$^{-/-}$) were bred in our animal facility. These mice do not express any Fmr1 protein and lack detectable Fmr1 transcripts. For all experiments, Fmr1$^{-/-}$ mice were used with wild-type littermates as a control group. The offspring were used for experiments at E18, P0, P2, P4, P7, P9, P15 and P30. Experiments were carried out on offspring of either sex and in a blind manner at E18 and P0.

Slice Preparation

Experiments were performed on fetuses and neonatal wild type and Fragile X mice from the embryonic day E20 to the postnatal day P38 (term is E21). All of the research was performed in compliance with the national guidelines on human care and use of laboratory animals and approved by INSERM.

Hippocampal slices (300-500 µm thick) were prepared using a Microm tissue slicer (International GmbH, Germany) as described previously (Tyzio et al., 2006, 2008). Slices were kept in oxygenated (95% $O_2$/5% $CO_2$) artificial cerebrospinal fluid (ACSF) of the following composition (in mM): NaCl 126, KCl 3.5, $CaCl_2$ 2.0, $MgCl_2$ 1.3, $NaHCO_3$ 25, $NaH_2PO_4$ 1.2 and glucose 11 (pH 7.4) at room temperature (20-22° C.) at least 1 hour before use.

Electrophysiology

For recordings, slices were placed into a conventional fully submerged chamber superfused with ACSF at a rate of 2-3 ml/min at room temperature. Patch clamp recordings from visually identified CA3 pyramidal cells in cell-attached configuration were performed using EPC-10 amplifier (HEKA Elektronik Dr. Schulze GmbH, Lambrecht/Pfalz, Germany). Patch pipette solution for recordings of single $GABA_A$ channels contained (in mM): NaCl 120, KCl 5, TEA-Cl 20, 4-aminopyridine 5, $CaCl_2$ 0.1, $MgCl_2$ 10, glucose 10, Hepes-NaOH 10 buffered to pH 7.2-7.3 and GABA 2 µM. Analysis of currents through single channels and current-voltage relationships were performed using Clampfit 9.2 (Axon Instruments, Union City, Calif.). Recordings were digitized (10 kHz) online with Digidata-1200 interface card (Axon Instruments, Union City, Calif.) and analyzed offline with Axon package, MiniAnalysis (S (Synaptsoft, Decatur, Ga.), and Origin (Microcal Software, Northampton, Mass.).

Whole-Cell Recordings

Standard whole-cell recordings were performed in coronal neocortical rat or mouse brain slices at room temperature (20-22° C.) from the soma of hippocampal CA3 neurons using an EPC-10 (HEKA Elektronik, Germany) amplifier and filtered at 3-10 kHz. The internal solution contained (in mM): 130 K-gluconate, 10 Na-gluconate, 4 NaCl, 4 MgATP, 4 phosphocreatine, 10 HEPES, and 0.3 GTP (pH 7.3 with KOH). Biocytin (final concentration 0.3-0.5%) was added to the pipette solution to label the neurons from which recordings were obtained. Neurons were visualized by using infrared DIC video microscopy. Spontaneous postsynaptic currents were recorded for 15 mM at the reversal potentials for GABAergic currents (−70 mV). It should be specifically noted that all recordings were made in normal ACSF (1.3 mM $MgCl_2$). Stored data were analyzed using the Mini Analysis 6.0.3 (Synaptsoft Inc., Chapell Hill, N.C.) and Origin (MicroCal, Northampton, Mass.) software. To minimize potential sampling bias, the pups from at least three deliveries for each condition were studied. Data are expressed as mean±S.E.M.

Extracellular Field Potentials and Multi-Unit Activity (MUA) Recordings

Recording were made in the hippocampal slices using tungsten wire electrodes (diameter: 50 µm, California Fine Wire, Grover Beach, Calif.) and a low-noise multichannel DAM-8A amplifiers (WPI, GB; low-pass filter: 0.1 Hz; high-pass filter: 3 KHz; gain: ×1000). The signals were digitized using an analogue-to-digital converter (Digidata 1440A, Axon Instruments, USA). pCLAMP 10.1, Clampfit 10.1 (Axon Instruments, USA), MiniAnalysis 6.03 (Synaptosoft, Decatur, Calif.) and Origin 7.5 (Microcal Software, USA) programs were used for the acquisition and analysis of the synaptic activities. Sampling interval per signal was 100 microseconds (10 kHz).

Vocalization

To induce ultrasonic vocalizations, mouse pups were isolated individually from their mother on postnatal day 8, and were placed into an isolation box (23×28×18 cm) located inside a sound attenuating isolation cubicle (54×57×41 cm; Coulbourn Instruments, Allentown, Pa., USA), and evaluated for ultrasonic vocalizations during a three minute test. An ultrasound microphone (Avisoft UltraSoundGate Condenser microphone capsule CM16/CMPA, Avisoft Bioacoustics, Berlin, Germany), placed in the roof of the box, was sensitive to frequencies of 10 to 250 kHz. Vocalizations were recorded using the Avisoft Recorder software (version 4.2) with a sampling rate of 250 kHz in 16 bit format. For acoustical analysis, recordings were transferred to SASLab Pro (version 5.2; Avisoft Bioacoustics) and a fast Fourier transformation was conducted (512 FFT-length, 100% frame, Hamming window and 75% time window overlap). The accuracy of call detection was verified manually by an educated user. A Pearson correlation coefficient was computed to assess the relationship between Automatic and Manual analysis. There was 0.99 correlations between the two variables. At postnatal day 8, waveform patterns of calls were examined in 45 sonograms from 4 groups of mice (WT, FXS, WT pretreated, FXS pretreated). Each call was identified as one of 10 distinct categories, and only the sonograms where mice emitted at least 50 calls were used for this evaluation.

Statistics

Group measures are expressed as means±SEM; error bars also indicate SEM. The statistical significance of differences was assessed with the Students t-test. The level of significance was set at $P<0.05$.

Pharmacology

All drugs were purchased from Sigma.

Results

Example 1: Developmental Excitatory/Inhibitory GABA Sequence is Abolished in Hippocampal CA3 Pyramidal Neurons in FXS Mice Delivery is associated with an oxytocin mediated reduction of intracellular chloride ($[Cl^-]_i$) leading to an excitatory to inhibitory shift of GABA action (Tyzio et al., 2006). This transient inhibitory shift during delivery exerts a neuroprotective action on central neurons reducing the sequels of anoxic episodes. Here, we analysed this shift in mouse model of fragile X syndrome (FXS).

To determine the driving force for $[Cl^-]_i$ (farther driving force of GABA ($DF_{GABA}$)), we used non-invasive single GABA$_A$ channel recordings in embryonic and post-natal hippocampal slices (E20 to P37) from animal models of FXS. In naive age matched and in heterozygote mice, DF$_{GABA}$ followed a sequence described in rats (Tyzio et al., 2006)—but not in mice—with an elevated [Cl$^-$]$_i$ and depolarising DF$_{GABA}$ in utero (E20) followed by an abrupt transient oxytocin mediated reduction of [Cl$^-$]$_i$ and depolarizing to hyperpolarizing shift of GABA actions restricted to a couple of hours before and after delivery (FIG. 1A, B; Table 1).

TABLE 1

Developmental changes of driving force of GABA in heterozygote (control) mice and FXSs. The data correspond to the graph on FIG. 1A.

| Age | Type | Mean DF$_{GABA}$, (pA) | ±SE | n | Condition |
|---|---|---|---|---|---|
| E20 | Wild-type | 16.5 | 2.04 | 6 | ACSF |
| E20 | FXS | 16.1 | 1.6 | 5 | ACSF |
| P0 | Wild-type | −2.5 | 0.9 | 54 | ACSF |
| P0 | FXS | 5.7 | 1.3 | 32 | ACSF |
| P7 | Wild-type | 12.7 | 1.2 | 24 | ACSF |
| P7 | FXS | 15.7 | 1.2 | 24 | ACSF |
| P14 | Wild-type | 6.8 | 1.1 | 15 | ACSF |
| P14 | FXS | 15.3 | 2 | 24 | ACSF |
| P28-37 | Wild-type | −0.04 | 1.4 | 8 | ACSF |
| P28-37 | FXS | 5.5 | 8.9 | 20 | ACSF |

Subsequently, GABA again depolarised neurons until P7, followed by a progressive decrement leading to the adult type action where DF$_{GABA}$ is close to the resting membrane potential (FIG. 1; Table 1). Therefore, in naive rat and mice neurons, DF$_{GABA}$ is strongly hyperpolarising immediately after birth but depolarising before and during the first post-natal week.

In contrast, in age matched FXS neurons, DF$_{GABA}$ remained depolarising from E20 to P28-37 with no significant difference between various ages (FIG. 1A) indicating that the curve is abolished including the delivery transient reduction. More precisely, in FXS neurons, we observed depolarising DF$_{GABA}$ in embryonic and P7 naive and FXS neurons but significantly more depolarised at other ages (FIG. 1A; Table 1). Applications of oxytocin (1 µM) shifted DF$_{GABA}$ during the delivery period (P0) in FXS neurons suggesting that oxytocin receptors are operative (FIG. 1C, Table 2).

TABLE 2

Changes of driving force of GABA in CA3 pyramidal cells from hippocampal slices from P0 wild type and FXS mice in presence of bumetanide and oxytocin. The data correspond to the graph on FIG. 1C.

| Age | Type | Mean DF$_{GABA}$, (pA) | ±SE | n | Condition |
|---|---|---|---|---|---|
| P0 | Wild-type | −2.5 | 0.9 | 54 | ACSF |
| P0 | Wild-type | −9.9 | 2.4 | 8 | Bumetanide |
| P0 | FXS | 5.7 | 1.3 | 32 | ACSF |
| P0 | FXS | −6.7 | 1.4 | 20 | Bumetanide |
| P0 | FXS | −8.8 | 1.6 | 14 | Oxytocin |

The NKCC1 chloride importer antagonist bumetanide that reduces [Cl$^-$]$_i$ fully blocked the depolarising DF$_{GABA}$ in FXS neurons at birth confirming the chronic persistent deregulation of chloride transport in autism (FIG. 1C, Table 2).

Present results provide the first demonstration of a permanent [Cl$^-$]$_i$ regulation deficiency in FXS lending experimental support to the successful therapeutic actions of bumetanide & oxytocin that reduce [Cl$^-$]$_i$.

Example 2: Maternal Pretreatment with Bumetanide in FXS Mice In Vitro

Figure 2:
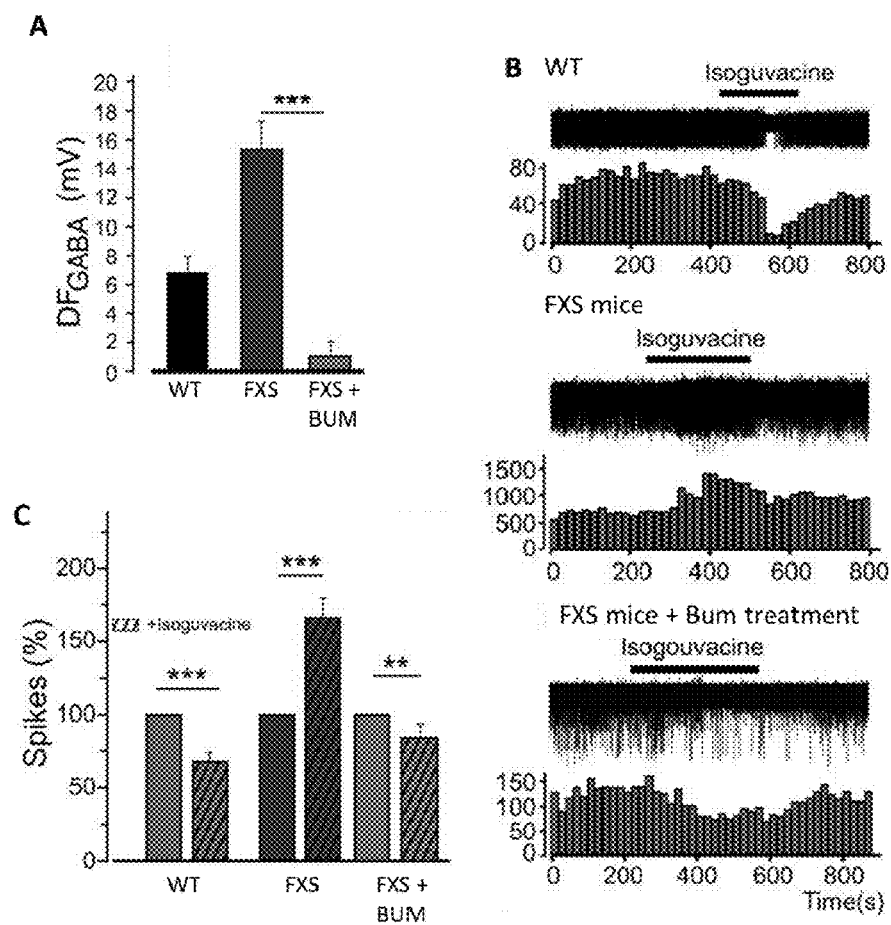
FIG. 2 represents in (A) histograms of average values of $DF_{GABA}$ measured in hippocampal CA3 pyramidal neurons at P15. WT mice ($6.8\pm1.1$ mV, n=15), FXS mice ($15.3\pm1.9$ mV, n=24) and FXS mice pretreated with bumetanide ($1.0\pm1.1$ mV, n=17, *$P<0.001$). (B) shows effects of isoguvacine (10 μM) in rats: Representative traces of spontaneous extracellular field potentials recorded in hippocampal slices at P15 in control, FXS mice and FXS mice pretreated with Bumetanide. Corresponding time-courses of spike frequency changes are shown under each trace. (C) shows average histograms of normalized spike frequency in mice shows WT mice (decrease to $67.9\pm6.1\%$ n=11, *$P<0.001$); FXS mice (increase to $165.8\pm13.5\%$, n=11, *$P<0.001$); FXS mice pretreated with bumetanide (decrease to $80.8\pm8.2\%$, n=5, *$P<0.05$). Two-tails t-test for all data sets. Data presented as means±S.E.M.
Figure 3:
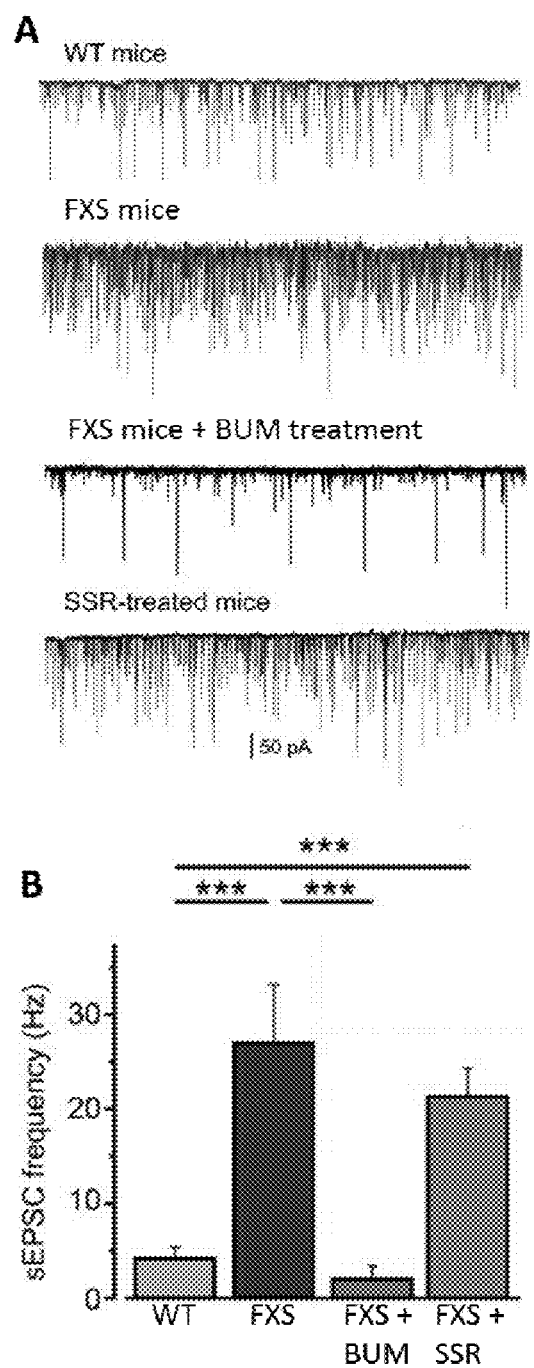
FIG. 3 represents whole-cell voltage clamp recordings of spontaneous excitatory postsynaptic currents (sEPSCs) at −70 mV from individual hippocampal CA3 pyramidal neurons in acute brain slices from P15 FXS mice and respective control and bumetanide or SSR pretreated animals. (A) shows representative traces of sEPSCs recorded from mice. (B) shows average values±S.E.M of sEPSCs frequencies in mice. WT mice (n=12) and FXS mice (n=9, *$P<9\times10^{-5}$), and FXS mice with maternal pretreatment with bumetanide (n=11, *$P<2.2\times10^{-5}$) and SSR-treated mice (n=13, ***$P<4.5\times10^{-5}$). One-way ANOVA Fisher's LSD post-hoc test. Data presented as means±S.E.M.

To test whether depolarizing actions of GABA were associated with neuronal excitation, the effect of the GABA$_A$ receptor agonist isoguvacine was tested. In naive neurons the specific GABA$_A$R agonist isoguvacine (2 µM) inhibited or did not affect field potential recordings at P15 (FIGS. 2B and C). To test whether maternal treatment with bumetanide before delivery switches the action of GABA from excitatory to inhibitory in offsprings at P15, pregnant females were treated orally 1 day before delivery with bumetanide (2-2.5 mg/kg in drinking water) and juvenile offspring neurons recorded at P15. Maternal pretreatment of FXS with bumetanide restored control DF$_{GABA}$ values in offsprings at P15 (FIG. 2A) suppressed the excitatory actions of the GABA$_A$R agonist isoguvacine (FIGS. 2 B and C) and significantly reduced ongoing activity and frequency of whole-cell recorded glutamatergic sEPSCs (FIG. 3). Therefore, excitatory actions of GABA during delivery produce long term deleterious effects on electrophysiological parameters of FXS juvenile neurons. In FXS mice, GABAergic inputs are excitatory and contribute to hyperexcitability of the network. Bumetanide decreases [Cl$^-$]$_i$ and consequently reduces contribution of excitatory GABAergic inputs in the overall network activity.

Example 3: Maternal Pretreatment with Bumetanide Restores Behavior of FXS Mice

Figure 4:
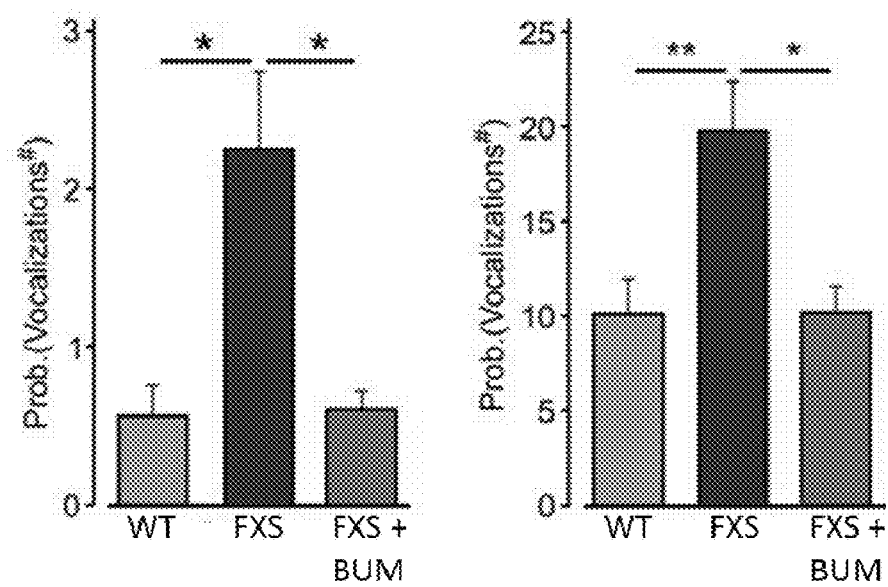
FIG. 4 represents isolation-induced ultrasonic vocalizations (USVs) in P8 WT (n=12), FXS (n=11) and FXS mice with maternal bumetanide pretreatment (n=13). One-way ANOVA Kruskal-Wallis test, Dunn's Multiple Comparison post-hoc test *$P<0.05$, **$P<0.01$.

Isolation and Ultrasonic vocalizations were induced in mice to determine behavioral effect of Bumetanide in a model of FXS. An increased probability of emitting downward and chevron calls in FXS pups than age matched WT (P8). This was rescued by maternal bumetanide pretreatment (FIG. 4, table 3). Therefore, elevated [Cl$^-$]$_i$ levels during delivery are involved in the pathogenesis of Fragile X syndrome.

TABLE 3 analysis of 10 types of calls in the FXS mouse model revealed an increased probability of emitting downward and chevron calls than age matched WT pups (P8).

| | Isolation-induced USVs mean ± S.E.M | |
|---|---|---|
| P8 | Chevron calls | Downward calls |
| WT mice | 0.6 ± 0.2 (n = 12) | 10.1 ± 1.8 (n = 12) |
| WT mice + BUM pretreatment | 0.5 ± 0.3 (n = 9) | 13.5 ± 2.8 (n = 9) |
| FXS mice | 2.3 ± 0.5 (n = 11) | 19.72 ± 2.6 (n = 11) |
| FXS mice + BUM pretreatment | 0.6 ± 0.1 (n = 13) | 10.2 ± 1.4 (n = 13) |
| Statistics | | |
| WT vs. FXS | P < 0.05 One-way ANOVA Kruskal-Wallis test, Dunn's Multiple Comparison post-hoc test | P < 0.01 One-way ANOVA Kruskal-Wallis test, Dunn's Multiple Comparison post-hoc test |
| FXS vs. FXS + BUM pretreatment | P < 0.05 One-way ANOVA Kruskal-Wallis test, Dunn's Multiple Comparison post-hoc test | P < 0.05 One-way ANOVA Kruskal-Wallis test, Dunn's Multiple Comparison post-hoc test |
| WT vs. WT + BUM pretreatment | n.s. Mann-Whitney test | n.s. Mann-Whitney test |

One-way ANOVA Kruskal-Wallis test, with Dunn's Multiple Comparison post-hoc test, and Mann-Whitney test.

Example 4: Clinical Study

This example is a case reports presenting the treatment by bumetanide of a 10-years boy with Fragile X syndrome.

The child was a bilingual boy born in October 2002 from Ukrainian mother and French father. He was the first child and had a younger sister. After a normal maternity, delivery came without difficulties (at birth, weight: 3.335 kg, length: 50.5 cm and head circumference: 36 cm). He was hospitalized at 2 to 8 days post-natal for a spontaneously resorbed hypotonia, his transfontanel cranial ultrasound examination was normal. He was breast-fed during 3 months, sat at 10 months, walked at 19 months, and acquired bladder control at 29 months for daytime and at 36 months for night-time. He had surgical treatment of inguinal hernia (right side) at 10 months and slope right foot treated by physiotherapy. During the spring 2004, the boy presented a malaise when swimming with his father with a sudden generalized tension followed with a brief (a few seconds) spontaneous episode of hypotonia and an empty gaze. Normal EEG was observed during wakefulness.

The first concerns of the parents came at 2 years because of an onset delay of speech. The child was frequently excited, seemed very anxious, scratched, felt and smelled objects, and refused physical contact and hugs. The absence of interactions with other children was noted at day care center. He was then admitted in a daily child and adolescent psychiatry service in May 2005 (3 half days weekly) until September 2010. Speech rehabilitation was initiated in May 2007. Admitted in kindergarten starting in September 2005, he repeated a year in 2008 and was then accompanied by a special needs assistant before being admitted in specialized institution (French structures named CLIS and IME).

In February 2008, a pediatric consultation noted a fin and elongated face. At the same time, a diagnosis of pervasive development disorder was made. It was noticed that he used intermittently language with some correct sentences but most often followed by words without links to the context. Another EEG test in March 2008 revealed no abnormality during the day (sleep recording was not possible). A second pediatric consultation revealed hyperactivity, many non-constructive manipulations and behavioral stereotypes (e.g. trolling a telephone for years). He slept readily but had frequent night-time awakenings. Following these repeated sleeping problems, the child received a melatonin treatment (2 mg at night) that ameliorated sleep cycles and reduced night-time awakenings. At this moment, communication became essentially echolalic. Genetic exploration with karyotype and specific research of Fragile X syndrome (FXS) was made in May 2008. A positive identification of FXS mutation was found.

A completed diagnosis was made at the Centre de Ressources de Bretagne (CRA) in June 2009. Psychomotor examination revealed an axial hypertonicity contrasting with a hypotonia associated with a hypermobility of the hands and feet, difficulty to appreciate height and deepness, absence of lateralization, difficulties in equilibrium and inadequate tonicity. Speech-language pathology was conspicuous that was more pronounced for words of more than syllables, a fast speech flow that handicapped intelligibility. Semantic tests revealed a delay of 3 years with important syntax troubles. The child using essentially isolated words and short verbal expressions, spontaneous sentences were rare and limited to various requests. The Wechsler scale (WPPSI III) was made. Performance IQ was 50 and verbal IQ was 56. During the tests, he explored the environment and objects with an emphasis on smell and hearing sensory modalities. There were clear social interactions deficits, for example the boy was unable to develop relations with his peers and to share pleasure intents, presenting great difficulties with socio-emotive reciprocity.

Starting from the 5 Jan. 2011, the child received bumetanide twice a day (0.5 mg morning and 0.5 mg evening) during three months. Several biological tests were made at baseline (D0) and then after 7 days (D7), one month (M1), two months (M2) and three months (M3) of treatment. They checked orthostatic hypotension, allergy, cramps, asthenia, diarrhea, myalgia, arthralgia, vertigo and nausea. Blood tests included γ-glutamyltransferase, transaminases, alkaline phosphatases, glycemia, uric acid and creatine, in addition to blood $Na^+$ and $K^+$.

Five clinical tests were made at baseline (D0) and after three months of treatment (M3) to determine the possible therapeutic efficacy including:

Efficacy of the treatment was measured at baseline (D0) and after three months of treatment (M3) using the GRAM scale (Grille Regulation Adaptation Modulation) for analyzing the dysregulation of the activity in a child; the ABC scale (Aberrant Behavior Checklist) for assessing problem behaviors of children and adults with mental retardation; and the CGI scale (Clinical Global Impression) for assessing the clinical amelioration in a patient following a therapeutic treatment.

After 90 days of treatment, ABC results reduced from 41 to 27. Moreover, GRAM results were reduced from 56 to 31. Finally, CGI result was 2, revealing a strong amelioration of the clinical state of the patient.

There was no side effect in the clinical examination made (i.e. orthostatic hypotension, allergy, cramps, asthenia, diarrhea, myalgia, arthralgia, vertigo and nausea). Conventional blood tests were also unaffected (i.e. γ-glutamyltransferase, transaminases, alkaline phosphatases, glycemia, uric acid, creatine).

Table 4 shows that body weight was not altered and blood $Na^+$ and remained stable. $K^+$ was reduced to a value close to the inferior limit (3.5 mmol/l). Natremia was unaltered by the treatment.

TABLE 4

Weight and blood ions during the 3 months of treatment.

| | Baseline ($D_0$) | 7 days ($D_7$) | 1 month ($M_1$) | 2 months ($M_2$) | 3 months ($M_3$) |
| --- | --- | --- | --- | --- | --- |
| $Na^+$ | 141 mmol/l | 143 mmol/l | 139 mmol/l | 140 mmol/l | 139 mmol/l |
| $K^+$ | 4.1 mmol/l | 3.6 mmol/l | 4.3 mmol/l | 3.5 mmol/l | 3.6 mmol/l |
| Weight | 25 kg | 25.2 kg | 25.1 kg | 25.4 kg | 25.7 kg |

Notice that bumetanide treatment continued after 3 months. $K^+$ was reduced to the inferior limit value, thus potassium gluconate syrup was added (i.e. one bulb morning and evening), starting from the 17 May 2011 (4th month of treatment). It led to a recuperation of normal K$^+$ (3.71 mmol/1) one month later (i.e. 11 Jun. 2011).

Taken together, these results show the efficacy of bumetanide for the treatment of Fragile X syndrome.

The invention claimed is:

1. A method for reducing or eliminating one or more symptom associated with Fragile X syndrome in a subject diagnosed with Fragile X syndrome, said method comprising the administration to the subject of an effective amount of a modulator of a chloride transporter, wherein said modulator is at least one inhibitor of NKCC selected from the group consisting of bumetanide and an analog thereof,
wherein said analog is selected from the group consisting of: bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)n-1-ethyl ester, bumetanide benzyltrimethyl-ammonium salt, bumetanide cetyltrimethylammonium salt, pivaloyloxymethyl ester of bumetanide, methyl ester of bumetanide, N,N-dimethylaminoethyl ester of bumetanide, bumetanide [—(C═O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S—(N,N-diethylglycolamido) thioester, bumetanide S—(N,N-dimethylglycolamido) thioester, bumetanide S-pivaxetil thioester, bumetanide S-propaxetil thioester, bumetanide S-(methoxypolyethyleneoxy)n-1-ethyl thioester, bumetanide [—(C═0)-S-] benzyltrimethyl-ammonium thioacid salt, bumetanide [—(C═O)—S] cetyltrimethylammonium thioacid salt, metastable bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl) thioester, bumetanide O-[3-(dimethylaminopropyl)] thioester, bumetanide O—(N,N-diethylglycolamido) thioester, bumetanide O-pivaxetil thioester, bumetanide O-propaxetil thioester, bumetanide O-[methoxy(poryethyleneoxy)n-1 ethyl] thioester, bumetanide [—(C═S)—O-] benzyltrimemyl-ammonium thioacid salt and bumetanide [—(C═S)—O-] cetyltrimethylammonium thioacid salt.

2. The method according to claim 1, wherein the effective amount ranges from about 0.01 mg to about 500 mg.

3. The method according to claim 1, wherein the modulator is administered to the subject by subcutaneous, intramuscular, intravenous, intraocular, transdermal, topical, parenteral, intranasal or oral administration or injection.

4. The method according to claim 1, wherein the subject presents a number of CGG repeats in the 5'-UTR of FMR1 of at least 55.

5. The method according to claim 1, wherein the subject is a fetus or a child.

6. The method according to claim 1, wherein the subject is a fetus and the modulator is administered to his/her mother.

7. A method for inhibiting chloride importation into neurons of a subject affected by Fragile X syndrome, comprising administering to the subject a therapeutically effective amount of a compound which inhibits the importation of chloride into neurons by inhibiting a NKCC co-transporter,
wherein said inhibitor is at least one selected from the group consisting of bumetanide and an analog thereof, wherein said analog is selected from group consisting of bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)n-1-ethyl ester, bumetanide benzyltrimethyl-ammonium salt, bumetanide cetyltrimethylammonium salt, pivaloyloxymethyl ester of bumetanide, methyl ester of bumetanide, N,N-dimethylaminoethyl ester of bumetanide, bumetanide [—(C═O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S—(N,N-diethylglycolamido) thioester, bumetanide S—(N,N-dimethylglycolamido) thioester, bumetanide S-pivaxetil thioester, bumetanide S-propaxetil thioester, bumetanide S-(methoxypolyethyleneoxy)n-1-ethyl thioester, bumetanide [—(C═0)-S-] benzyltrimethyl-ammonium thioacid salt, bumetanide [—(C═O)—S] cetyltrimethylammonium thioacid salt, metastable bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl) thioester, bumetanide O-[3-(dimethylaminopropyl)] thioester, bumetanide O—(N,N-diethylglycolamido) thioester, bumetanide O-pivaxetil thioester, bumetanide O-propaxetil thioester, bumetanide O-[methoxy(poryethyleneoxy)n-1 ethyl] thioester, bumetanide [—(C═S)—O-] benzyltrimemyl-ammonium thioacid salt and bumetanide [—(C═S)—O-] cetyltrimethylammonium thioacid salt.

8. The method according to claim 1, wherein the at least one inhibitor of NKCC is bumetanide.

9. The method according to claim 1, wherein the effective amount ranges from about 0.5 mg to about 1.5 mg.

10. The method according to claim 1, wherein the effective amount ranges from about 0.5 mg/day to about 1.5 mg/day.

* * * * *